United States Patent
Egli et al.

(12)

(10) Patent No.: US 12,053,007 B2
(45) Date of Patent: Aug. 6, 2024

(54) USE OF NUTRITIONAL COMPOSITIONS HAVING A LOW PROTEIN AMOUNT

(71) Applicant: SOCIÉTÉ DES PRODUITS NESTLÉ S.A., Vevey (CH)

(72) Inventors: Delphine Egli, La Tour-de-Peilz (CH); Ferdinand Haschke, La Tour-de-Peilz (CH); Karl-Josef Huber-Haag, Pully (CH); Philippe Steenhout, La Tour-de-Peilz (CH); Sze Tan, Chardonne (CH)

(73) Assignee: Societe des Produits Nestle S.A., Vevey (CH)

( * ) Notice: Subject to any disclaimer, the term of this patent is extended or adjusted under 35 U.S.C. 154(b) by 82 days.

(21) Appl. No.: 17/576,202

(22) Filed: Jan. 14, 2022

(65) Prior Publication Data
US 2022/0132903 A1    May 5, 2022

Related U.S. Application Data

(62) Division of application No. 15/100,407, filed as application No. PCT/EP2013/075050 on Nov. 29, 2013, now Pat. No. 11,252,986.

(51) Int. Cl.
   A23L 33/20      (2016.01)
   A23L 33/00      (2016.01)
   A23L 33/125     (2016.01)
   A23L 33/135     (2016.01)
   A23L 33/19      (2016.01)

(52) U.S. Cl.
   CPC ............. *A23L 33/20* (2016.08); *A23L 33/125* (2016.08); *A23L 33/135* (2016.08); *A23L 33/19* (2016.08); *A23L 33/40* (2016.08); *A23V 2002/00* (2013.01)

(58) Field of Classification Search
   None
   See application file for complete search history.

(56) References Cited

U.S. PATENT DOCUMENTS

| 2010/0068149 A1 | 3/2010 | Zwijsen et al. |
| 2010/0092610 A1 | 4/2010 | Haschke et al. |
| 2011/0195144 A1 | 8/2011 | Haschke et al. |
| 2013/0079276 A1 | 3/2013 | Van Goudoever et al. |

FOREIGN PATENT DOCUMENTS

| WO | 2013057233 | 4/2013 |

OTHER PUBLICATIONS

Koletzko et al. "Lower protein in infant formula is associated with lower weight up to age 2y: a randomized clinical trial1-4" The American Journal of Clinical Nutrition, 2009, vol. 89, pp. 1836-1845.

*Primary Examiner* — Kyung S Chang
(74) *Attorney, Agent, or Firm* — K&L Gates LLP

(57) ABSTRACT

The present invention relates to the use of a nutritional composition having a low amount of protein, such as less than 1.8 g/100 kcal for administration to infants of non-obese and non-overweight mothers so as to reduce the risk of developing metabolic syndrome, increased weight gain, increased fat deposition, overweight, obesity, insulin resistance, glucose intolerance or diabetes mellitus later in said infant's life.

33 Claims, No Drawings

USE OF NUTRITIONAL COMPOSITIONS HAVING A LOW PROTEIN AMOUNT

CROSS REFERENCE TO RELATED APPLICATIONS

The present application is a divisional of U.S. patent application Ser. No. 15/100,407, filed on May 31, 2016, which is a National Stage of International Application No. PCT/EP2013/075050, filed on Nov. 29, 2013, the entire contents of which are being incorporated herein by reference.

TECHNICAL FIELD OF THE INVENTION

The present invention relates to the uses of a nutritional composition with a protein content less than 1.8 g/100 kcal to an infant born to a non-obese and non-overweight mother. In particular the present invention relates to the use of said nutritional composition for reducing the risk of an infant fed with said nutritional composition to develop metabolic syndrome, overweight, obesity, glucose intolerance or diabetes mellitus later in life. Furthermore, the present invention relates to the use of a nutritional composition to obtain a hormonal profile closer to that of breast fed infants, to reduce the protein burden on non-mature organs in the infant and to promote a rate of growth of the infant which approximates the rate of growth of a breast fed infant at the same age.

BACKGROUND OF THE INVENTION

Mother's milk is recommended for all infants up to the age of 4-6 months. However, in some cases breast feeding is inadequate or unsuccessful or inadvisable for medical reasons, or the mother chooses not to breast feed either at all or for a period of more than a few weeks. Infant formulas have been developed for these situations.

The prevalence of obesity and overweight in adults, children and adolescents has increased rapidly over the past 30 years in the United States and globally and it continues to rise. Overweight and obesity are classically defined based on the percentages of body fat or, more recently, the body mass index of BMI. The BMI is defined as the ratio of weight in kilograms divided by the height in metres, squared.

As overweight and obesity become more prevalent in all age groups, the number of women giving birth who are also overweight or obese is also increasing.

It is known that overweight and obese women who become pregnant have a greater risk of developing gestational diabetes. Maternal hyperglycaemia may lead to infants with increased body size and fat mass and such infants are themselves prone to develop obesity or diabetes later in childhood or in adult life. An increasing weight of scientific evidence suggests that infants born to obese mothers have a greater risk of becoming overweight or obese later in life than infants born to mothers who are not obese.

However, childhood obesity and overweight seem to be more and more common today, even though neither the mother nor the father of the child is obese. Childhood overweight and obesity currently affect 18 million children under the age of 5 worldwide. Almost 30% of US children and adolescents, and between 10 and 30% of European children are overweight or obese.

It is well known that infants fed with infant formula obtain a higher weight gain than breast fed infants. Infant formula fed infants may therefore be more prone to become overweight or obese later in life.

Hence, there is an unmet need for a nutritional composition to be used for administration to infants of non-obese and non-overweight mothers to reduce the risk of developing overweight, obesity, diabetes and metabolic syndrome later in life.

Further, there is a need for a nutritional composition to be used in feeding infants of non-obese and non-overweight mothers, said nutritional composition promoting a growth rate of the infant which approximates the growth rate of an infant being breast fed, i.e. normalizes the growth rate of an infant.

Further, infant formulas on the market today have a high content of proteins, which is higher than the protein content in the human breast milk. High amount of proteins may cause damage to non-mature organs in an infant. Thus, there is a need for an infant formula which may reduce the protein burden on non-mature organs in the infant.

SUMMARY OF THE INVENTION

Thus, an object of the present invention relates to the use of a nutritional composition for administration to an infant, wherein said nutritional compositions can reduce the risk of the infant to develop metabolic syndrome, overweight, obesity, glucose intolerance and diabetes mellitus later in said infant's life and can normalize the growth rate of the infant and reduce the protein burden on non-mature organs.

It is a further object of the present invention to use a nutritional composition for feeding infants in order to obtain a hormonal profile which is closer to that of breast fed infants.

In particular, it is an object of the present invention to provide a nutritional composition for use in administration to infants that solves the above mentioned problems with known nutritional compositions for infants such as infant formulas, since the known infants formulas have a high content of proteins and energy content which promotes a higher growth rate than breast fed children, a higher risk of obtaining obesity later in life and the damage of non-mature organs.

While obesity in childhood and adolescence is increasing to the point where it is starting to be of serious concern to healthcare professionals, there are many contributory factors to obesity, including nutritional, environmental and inherited factors. It is recognized that the likelihood of developing a nutritional product which is effective in reducing this risk of developing obesity in the infant population at large is remote. However, without being bound by any theory, the inventors of the present invention believe that it is possible to reduce the risk of future overweight or obesity by feeding an infant with a nutritional composition according to the invention.

As research into the composition of human milk continues, increasing attention is being paid to the extent to which its composition changes over the period of lactation. These changes are particularly pronounced as regards protein quality and quantity. Dietary protein provides the essential amino acids necessary for protein synthesis and growth. Nutritional compositions to be fed to infants are usually based on cows' milk but the amino acid profile of cows' milk is noticeably different from that of human milk which, in addition, has the lowest protein concentration found in any mammalian milk. In the past, in order to supply enough of the essential amino acids, infant formulas based on cows' milk had to have a protein content significantly higher than that of the human milk. More recently, it has been realised that the total protein quantity can be reduced whilst still meeting the minimum requirements for essential amino acids by a judicious selection of protein sources supplemented if necessary by small quantities of free amino acids.

However, this line of development does not take account of the physiological properties of particular proteins and the evolution of protein content of human milk over time. Human milk is generally considered to be whey predominant and a range of "whey-adapted" formulas have been developed based on this. However, this fails to take account of the fact that the casein to whey ratio (casein:whey) of human milk varies over time from 20:80 in the first few days of lactation to 50:50 after five to six months after lactation. Furthermore, the protein content of human milk is likewise not constant over time and may vary between 1.8 and 1.3 g/100 kcal depending upon the duration of lactation.

Earlier, a connection has been established between the protein content in an infant formula and infants having a high risk of developing obesity later in life, because they are born from mothers being obese before being pregnant. It was shown that by decreasing the protein content in infant formulas, the IGF-1 level in infants of obese mothers was decreased. It was not expected by anyone that this effect could also be seen for infants born to non-obese and non-overweight mothers, i.e. under weight or normal weight mothers.

However, the inventors of the present invention have surprisingly found out that when feeding an infant of a non-obese and non-overweight mother with a nutritional composition comprising a controlled amount of protein, i.e. less than 1.8 g/100 kcal protein, but still supplying sufficient quantities of other nutrients which are essential for growth and development, the IGF-1 level in the infant will decrease. Hereby is provided a hormonal profile closer to that of breast fed infants and the risk of the infant to develop obesity later in life is reduced. The infant will usually be fed with the nutritional composition according to the invention from the age of 3 months, since the need of proteins for an infant is higher immediately after birth, but decreases with age.

Further, the inventors of the present invention have surprisingly found out that the administration of a nutritional composition comprising a controlled amount of protein, i.e. less than 1.8 g/100 kcal protein, but still supplying sufficient quantities of other nutrients which are essential for growth and development, to an infant born to a non-obese and non-overweight mother will promote a growth rate in the infant which approximates to the growth rate which is observed in infants fed with human breast milk at the same age. Furthermore, by feeding infants with a low amount of proteins, such as less than 1.8 g/100 kcal, the protein burden on non-mature organs of the infant is reduced.

Thus, one aspect of the invention relates to a nutritional composition comprising a protein source, a lipid source and a carbohydrate source, wherein the protein content is less than 1.8 g/kcal for use in administration to an infant born to a non-obese and non-overweight mother in the first year of the life or the infant so as to reduce risk of developing metabolic syndrome, increased weight gain, increased fat deposition, overweight, obesity, insulin resistance or diabetes mellitus later in said infant's life.

Another aspect of the present invention relates to a nutritional composition comprising a protein source, a lipid source and a carbohydrate source, wherein the protein content is less than 1.8 g/100 kcal for use in administration to an infant born to a non-obese and non-overweight mother in the first year of the life of the infant so as to obtain a hormonal profile closer to that of breast fed infants.

Yet another aspect of the present invention relates to a nutritional composition comprising a protein source, a lipid source and a carbohydrate source, wherein the protein content is less than 1.8 g/100 kcal for use in for administration to an infant born to a non-obese and non-overweight mother in the first year of the life of the infant so as to reduce the protein burden on non-mature organs in the infant.

Still another aspect of the present invention is to provide a protein source, a lipid source and a carbohydrate source, wherein the protein content is less than 1.8 g/100 kcal for use in administration to an infant born to a non-obese and non-overweight mother in the first year of the life of the infant so as to promote a rate of growth in that infant which approximates to the rate of growth of a breast fed infant at the same age.

A further aspect of the present invention relates to the use of a protein source, a lipid source and a carbohydrate source for the preparation of a nutritional composition, wherein said composition comprises a protein content of less than 1.8 g/100 kcal for administration to an infant born to a non-obese and non-overweight mother in the first year of the life of the infant so as to reduce risk of developing metabolic syndrome, increased weight gain, increased fat deposition, overweight, obesity, insulin resistance or diabetes mellitus later in said infant's life.

Another aspect of the present invention relates to the use of a protein source, a lipid source and a carbohydrate source for the preparation of a nutritional composition, wherein said composition comprises a protein content of less than 1.8 g/100 kcal for administration to an infant born to a non-obese and non-overweight mother in the first year of the life of the infant so as to obtain a hormonal profile closer to that of breast fed infants.

Still a further aspect of the present invention relates to the use of a protein source, a lipid source and a carbohydrate source for the preparation of a nutritional composition, wherein said composition comprises a protein content of less than 1.8 g/100 kcal for administration to an infant born to a non-obese and non-overweight mother in the first year of the life of the infant so as to reduce the protein burden on non-mature organs in the infant.

Yet another aspect of the present invention relates to the use of a protein source, a lipid source and a carbohydrate source for the preparation of a nutritional composition, wherein said composition comprises a protein content of less than 1.8 g/100 kcal for administration to an infant born to a non-obese and non-overweight mother in the first year of the life of the infant so as to promote a rate of growth in that infant which approximates to the rate of growth of a breast fed infant at the same age.

A further aspect of the present invention relates to a method for reducing risk in an infant born to a non-obese and non-overweight mother to develop metabolic syndrome, increased weight gain, increased fat deposition, overweight, obesity, insulin resistance or diabetes mellitus later in said infant's life, the method comprising administering to said infant born to a non-obese and non-overweight mother, in the first year of the life of the infant, a nutritional composition comprising a protein source, a lipid source and a carbohydrate source and wherein said composition comprises a protein content of less than 1.8 g/100 kcal.

Another aspect of the present invention relates to a method for obtaining in an infant born to a non-obese and non-overweight mother a hormonal profile closer to that of breast fed infants, the method comprising administering to said infant born to a non-obese and non-overweight mother, in the first year of the life of the infant, a nutritional composition comprising a protein source, a lipid source and a carbohydrate source and wherein said composition comprises a protein content of less than 1.8 g/100 kcal.

Still a further aspect of the present invention relates to a method for reducing the protein burden on non-mature organs in an infant born to a non-obese and non-overweight mother, the method comprising administering to said infant in the first year of the life of the infant a nutritional composition comprising a protein source, a lipid source and a carbohydrate source and wherein said composition comprises a protein content of less than 1.8 g/100 kcal.

Yet another aspect of the present invention relates to a method for promoting a rate of growth in an infant born to a non-obese and non-overweight mother which approximates to the rate of growth of a breast fed infant at the same age, the method comprising administering to said infant born to a non-obese and non-overweight mother, in the first year of the life of the infant, a nutritional composition comprising a protein source, a lipid source and a carbohydrate source and wherein said composition comprises a protein content of less than 1.8 g/100 kcal.

The present invention will now be described in more details.

DETAILED DESCRIPTION OF THE INVENTION

Definitions

Prior to discussing the present invention in further details, the following terms and conventions will first be defined:

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth. All references to singular characteristics or limitations of the present invention shall include the corresponding plural characteristic or limitation, and vice versa, unless otherwise specified or clearly implied to the contrary by the context in which the reference is made.

In the context of the present invention, the term "ratio" by weight (weight/weight) refers to the ratio between the weights of the mentioned compounds. For example, a mixture comprising 60 g whey and 40 g casein would have a weight ratio which is equal to 60:40, which is equal to 3:2 or 1.5 (that is 3 divided with 2). Similarly, a mixture of 50 g whey and 50 g casein would have a ratio by weight of whey and casein of 50:50, which is equal to 1:1 or 1 (that is 1 divided with 1).

The term "and/or" used in the context of the "X and/or Y" should be interpreted as "X", or "Y", or "X and Y".

Unless defined otherwise, all technical and scientific terms used herein have the same meaning as commonly understood by one of ordinary skill in the art.

The term "infant" will in the context of the present invention mean a child under the age of 2 years, preferably the infant is a child under the age of 12 months.

In the context of the present invention, the infant may be any term infant or preterm infant. In an embodiment of the invention, the infant is selected from the group of preterm infants and term infants.

The "nutritional composition" can be a synthetic nutritional composition, i.e. not of human origin (e.g. this is not breast milk). It can be an infant formula, a starter infant formula, a follow-on formula, an infant cereal, a fortifier such as a human milk fortifier, or a supplement. In a particular embodiment, it is an infant formula.

The expression "synthetic composition" means a mixture obtained by chemical and/or biological means, which can be chemically identical to the mixture naturally occurring in mammalian milks.

The term "infant formula" as used herein refers to a nutritional composition intended for infants and as defined in Codex Alimentarius, (Codex STAN 72-1981) and Infant Specialities (incl. Food for Special Medical Purpose) as defined in Codex Alimentarius, (Codex STAN 72-1981). It also refers to a foodstuff intended for particular nutritional use by infants during the first months of life and satisfying by itself the nutritional requirements of this category of person (Article 2(c) of the European Commission Directive 91/321/EEC 2006/141/EC of 22 Dec. 2006 on infant formulae and follow-on formulae). The infant formulas can encompass the starter infant formulas and the follow-up or follow-on formulas. Generally a starter formula is for infants from birth as breast-milk substitute, and a follow-up or follow-on formula from the 6th month onwards.

The expressions "later in life" or "later in said infant's life" refer in the context of the present invention to effects measured in the child after the age of 1 year of life, such as after the age of 2 years, preferably after the age of 4 years, such as after the age of 5 years, even more preferably after the age of 7 years of life and as a comparison to average observations for subjects of the same age, but not having the same conditions because fed with another nutrition.

The term "normal growth rate of a breast fed infant" means the growth rate for breast fed infants set out in Acta Oaediatrica, Vol 95, April 2006, Supplement 450 "WHO Child Growth Standards".

"Rate of growth" refers to growth in weight, height, head circumference of an infant.

The term "obese mother" means a woman with a BMI of at least 30 prior to establishment of pregnancy.

The term "overweight mother" means a woman with a BMI between 25 and below 30 prior to establishment of pregnancy.

The term "normal weight mother" means a woman with a BMI between 18.5 and below 25 prior to establishment of pregnancy.

The term "underweight mother" means a woman with a BMI below 18.5 prior to establishment of pregnancy. This expression encompasses the "severely underweight" mothers, i.e. mothers with a BMI less than 16.5.

The term "non-obese mother" means a woman with a BMI below 30 prior to establishment of pregnancy.

In the present invention, the infant is born to "a non-obese and non-overweight mother". This means that the infant is born to a mother who is neither obese nor overweight prior to establishment of pregnancy. It therefore means that the infant is born to a mother with a BMI below 25 prior to establishment of pregnancy. The "non-obese and non-overweight mother" will be either a "normal weight mother", i.e. a mother with a BMI between 18.5 and below 25 prior to establishment of pregnancy, or an "underweight mother", i.e. a mother with a BMI below 18.5 prior to establishment of pregnancy.

BMI refers to body mass index and is a measure for weight. BMI is defined as the ratio of weight in kilograms divided by height in metres, squared.

An infant born to an obese or an overweight mother will have different physiological conditions than an infant born to a non-obese and non-overweight mother. The reason for this is that maternal obesity will cause that the foetus is developed in an insulegenic environment. This causes a gestational weight gain, elevated adiposity, hyperglycemia and insulin resistance in the infant of the obese mother. Thus, infants of obese mothers will have an increased risk of childhood obesity and subsequent adult diseases, such as diabetes. Infants of overweight mothers may have some of the symptoms described above (but in a less degree). An infant from a non-obese and non-overweight mother will not have the symptoms described above. Infants of normal weight mothers and underweight mothers do not have any of the described symptoms, since their gestational development has not been in an increased insulinogenic environment.

The term "protein content" means total content of proteinaceous material including free amino acids (if present).

All percentages and ratios are by weight unless otherwise specified.

The term "hormonal profile" refers in the context to the content of hormones present in the blood of an infant, e.g. the amounts of IGF-1 measured in the blood of an infant.

The term "IGF-1" refers to the hormone "insulin-like growth factor-1".

The expressions "non-mature organs", "unmature organs" and "immature organs" can be used interchangeably.

Energy Density:

The energy density of the nutritional composition according to the present invention is specified as the number of kilocalories per litre (kcal/l). Furthermore, the energy density refers in the context of powdered products, to the product after reconstitution according to the directions provided with the product.

The term "energy density" may also be termed "caloric density". The terms may be used interchangeably.

In an aspect of the invention, the energy density of the nutritional composition according to the invention is less than 680 kcal/l, such as from 600 to 680 kcal/l, such as from 620 to 680 kcal/l, such as from 620 to 650 kcal/l, particularly 620 kcal/l or particularly 640 kcal/l. In some embodiments the energy density may also be from 650 to 680 kcal/l, particularly 670 kcal/l.

Proteins:

In the context of the present invention, the term "protein" refers to both proteins derived from a source of protein, peptides and to free amino acids in general. Furthermore, the term "protein" refers to one or more proteins.

The nutritional composition of the present invention has a protein content of less than 1.8 g/100 kcal.

In an embodiment of the invention the protein content is between 1.4 and 1.75 g/100 kcal, such as between 1.4 and 1.7 g/100 kcal, between 1.5 and 1.7 g/100 kcal, or between 1.5 and 1.65 g/100 kcal, or between 1.5 and 1.6 g/100 kcal. In a particular embodiment the protein content is 1.61 g/100 kcal.

In a particular embodiment the protein content is 1.69 g/100 kcal. In some particular embodiments the protein content is between 1.6 and 1.75 g/100 kcal such as between 1.6 and 1.75 g/100 kcal, or between 1.61 and 1.69 g/100 kcal.

The detailed make-up of the protein source is not believed to be critical to the present invention provided that the minimum requirements or essential amino acid content are met and satisfactory growth is ensured. However, in a particular embodiment of the invention the protein sources are based on cow's milk proteins such as whey, casein and mixtures thereof. Furthermore, protein sources based on soy can be used. In an embodiment of the invention, the protein is selected from the group of milk proteins, animal proteins, vegetable proteins, cereal proteins, free amino acids or combinations thereof. The milk protein advantageously includes casein and/or whey protein.

In an embodiment of the invention, the protein source comprises at least 20% of casein, such as at least 25% casein, e.g. at least 30% casein, or at least 35% casein, such as at least 40% casein.

In an embodiment of the invention, the protein source comprises at least 20% of whey, such as at least 30% whey, such as at least 40% whey, or at least 50% whey, such as at least 55% whey, particularly at least 60% whey.

In another embodiment of the invention the protein is made of mixtures of casein and whey proteins. The casein to whey ratio is typically in the range of 0:100 to 50:50, such as 30:70 to 70:30, such as 40:60 to 60:40, in particular 45:55 to 40:60, and advantageously 40:60.

In a particular embodiment there is no casein but 100% of whey.

The protein(s) in the protein source may be intact or partially hydrolysed or a combination of intact and hydrolysed proteins.

In an embodiment of the invention, the protein(s) in the protein source is hydrolysed.

In another embodiment of the invention, the protein(s) in the protein source is intact.

The term "intact" means in the context of the present invention proteins where the molecular structure of the protein(s) is not altered according to conventional meaning of intact proteins. By the term "intact" is meant that the main part of the proteins are intact, i.e. the molecular structure is not altered, for example at least 80% of the proteins are not altered, such as at least 85% of the proteins are not altered, e.g. at least 90% of the proteins are not altered, or at least 95% of the proteins are not altered, such as at least 98% of the proteins are not altered. In a particular embodiment, 100% of the proteins are not altered.

The term "hydrolysed" means in the context of the present invention a protein which has been hydrolysed or broken down into its component peptides or amino acids.

The proteins may either be fully or partially hydrolysed. In an embodiment of the invention at least 70% of the proteins are hydrolysed, preferably at least 80% of the proteins are hydrolysed, such as at least 85% of the proteins are hydrolysed, even more preferably at least 90% of the proteins are hydrolysed, such as at least 95% of the proteins are hydrolysed, particularly at least 98% of the proteins are hydrolysed. In a particular embodiment, 100% of the proteins are hydrolysed.

Hydrolysis of proteins may be achieved by many means, for example by prolonged boiling in a strong acid or a strong base or by using an enzyme such as the pancreatic protease enzyme to stimulate the naturally occurring hydrolytic process.

The protein(s) according to the present invention may also be derived from free amino acids, or a combination of free amino acids and a source of protein, such as whey and casein. In some cases it might be necessary to supplement a source of protein with free amino acids, if it is necessary to meet the minimum requirements for essential amino acid content. These requirements are published for example in EC Directive 91/321/EEC.

As noted above, the protein source may be a mixture of casein and whey proteins.

The whey protein may be a whey protein isolate, acid whey, sweet whey or sweet whey from which the caseino-glycomacropeptide has been removed (modified sweet whey). Preferably, however, the whey protein is modified sweet whey. Sweet whey is a readily available by-product of cheese making and is frequently used in the manufacture of nutritional compositions based on cows' milk. However, sweet whey includes a component which is undesirably rich in threonine and poor in tryptophan called caseino-glycomacropeptide (cGMP). Removal of the cGMP from sweet whey results in a protein with a threonine content closer to that of human milk. A process for removing cGMP from sweet whey is described in EP880902.

If modified sweet whey is used as the whey protein in a mixture of 60% whey and 40% casein, the protein source is advantageously supplemented by free tryptophan, isoleucine, histidine and phenylalanine in amounts of up to 0.34% for tryptophan, 0.92% for isoleucine, 0.19% for histidine and 2.2% for phenylalanine (in each case as a percentage by weight of total protein content). If intact sweet whey is used as the whey protein in a mixture of 60% whey and 40% casein, the protein source is preferably supplemented by free tryptophan, leucine, histidine and phenylalanine in amounts of up to 0.5% for tryptophan, 0.73% for leucine, 0.3% for histidine and 2.5% for phenylalanine (in each case as a percentage by weight of total protein content).

In an embodiment of the present invention the whey protein is sweet whey from which the caseino-glycomacropeptide has been removed and the composition additionally includes free phenylalanine in an amount of up to 2.2%, free isoleucine in an amount of up to 0.92%, free tryptophan in an amount of up to 0.34% and free histidine in an amount of up to 0.19%, in each as a percentage by weight of total protein content. The above described protein of sweet whey has a good amino acid profile that is as close as possible to the amino acid profile of the human breast milk.

Carbohydrates:

The nutritional composition of the present invention contains a source of carbohydrates. The preferred source of carbohydrates is lactose although other carbohydrates such as saccharose, maltodextrin and/or starch may also be added. Advantageously, the carbohydrate content present in the nutritional composition is between 9 and 14 g/100 kcal.

In an embodiment of the invention, the carbohydrate source is lactose.

Lipids:

The nutritional composition of the present invention also contains a source of lipids. The lipid source may be any lipid or fat which is suitable for use in nutritional compositions to be fed to infants. Preferred fat sources include coconut oil, low erucic rapeseed oil (canola oil), soy lecithin, palm olein and/or sunflower oil. The essential polyunsaturated fatty acids linoleic acid and α-linolenic acid may also be added as small amounts of oils containing high quantities of preformed long chain polyunsaturated fatty acids arachidonic acid and docosahexaenoic acid, e.g. fish oils or single cell oils. In total, the lipid content may be between 4.4 and 6 g/100 kcal.

In an embodiment of the present invention, the ratio of linoleic acid (C18:2n-6) to α-linolenic acid (C18:3n-3) in the lipid source is between 5:1 to 15:1, advantageously between 7:1 and 15:1, such as 8:1.

In another embodiment of the present invention, the ratio of arachidonic acid (C20:4n-6) to docosahexaenoic acid (C22:6n-3) in the lipid source is between 2:1 and 1:1.

Vitamins and Minerals:

The nutritional composition may also contain all vitamins and minerals understood to be essential in the daily diet in nutritionally significant amounts. Minimum requirements have been established for certain vitamins and minerals. Examples of minerals, vitamins and other nutrients optionally present in the nutritional composition include vitamin A, vitamin B1, vitamin B2, vitamin B6, vitamin E, vitamin K, vitamin C, vitamin D, folic acid, inositol, niacin, biotin, pantothenic acid, choline, calcium, phosphor, iodine, iron, magnesium, copper, zinc, manganese, chloride, potassium, sodium, selenium, chromium, molybdenum, taurine, and L-carnitine. The minerals are usually added in salt form.

Emulsifiers:

If necessary, the nutritional composition may contain emulsifiers and stabilisers such as lecithin, e.g. soy lecithin, monoglycerides, diglycerides or citric esters of mono- and di-glycerides, and the like. This is especially the case if the composition is provided in liquid form and particularly if the content of lipids is high.

Compounds with Beneficial Effect:

The nutritional composition according to the present invention may optionally comprise other compounds which may have a beneficial effect such as probiotics (like probiotic bacteria), fibres, lactoferrin, nucleotides, nucleosides, and the like in the amounts customarily found in nutritional compositions to be fed to infants.

Strains of *Lactobacillus* are the most common microbes employed as probiotics. However, other probiotic strains than *Lactobacillus* may be used in the present nutritional composition, for example *Bifidobacterium* and certain yeasts and bacilli. The probiotic microorganisms most commonly used are principally bacteria and yeasts of the following genera: *Lactobacillus* spp., *Streptococcus* spp., *Enterococcus* spp., *Bifidobacterium* spp. and *Saccharomyces* spp.

In some particular embodiments, the probiotic is a probiotic bacterial strain. Probiotic bacteria are bacteria which have a beneficial effect on the intestinal system of humans and other animals.

In some specific embodiments, it is particularly Bifidobacteria and/or Lactobacilli.

In an embodiment of the invention, the nutritional composition further includes a probiotic strain such as a probiotic bacterial strain in an amount of from $10^6$ to $10^{11}$ cfu/g of composition (dry weight).

A probiotic is a microbial cell preparation or components of microbial cells with a beneficial effect on the health or well-being of the host. Suitable probiotic bacterial strains include *Lactobacillus rhamnosus* ATCC 53103 obtainable from Valio Oy of Finland under the trademark LGG, *Lactobacillus rhamnosus* CGMCC 1.3724, *Lactobacillus paracasei* CNCM I-2116, *Bifidobacterium lactis* CNCM 1.3446 sold by inter alia by the Christian Hansen company of Denmark under the trademark Bb12 and *Bifidobacterium longum* ATCC BAA-999 sold by Morigana Milk Industry Co. Ltd. of japan under the trademark BB536. The amount of probiotic, if present, likewise preferably varies as a function of the age of the infant.

Since probiotic bacteria have a beneficial effect on the intestinal flora in a human being, also an infant, it is believed by the inventors of the present invention, without being bound by any theory, that probiotic bacteria in a nutritional composition in combination with a low amount of proteins provide a synergistic effect to reduce the risk of an infant fed with said nutritional composition to obtain obesity later in life. Probiotics enable a better utilization of nutrients while producing by-products that may have a physiological effect on digestion. The use of specific probiotics can therefore improve the uptake and beneficial effect of a diet having a high amount of proteins.

The infant formula may also contain at least one prebiotic in an amount of 0.3 to 10%. A prebiotic is a non-digestible food ingredient than beneficially affects the host by selectively stimulating the growth and/or activity of one or a limited number of bacteria in the colon, and thus improves host health. Such ingredients are non-digestible in the sense that they are not broken down and absorbed in the stomach or small intestine and thus pass intact to the colon where they are selectively fermented by the beneficial bacteria. Examples of prebiotics include certain oligosaccharides, such as fructooligosaccharides (FOS) and galactooligosaccharides (GOS). The prebiotics can also be a BMO (bovine's milk oligosaccharide) and/or a HMO (human milk oligosaccharide) such as N-acetylated oligosaccharides, sialylated oligosaccharides, fucosylated oligosaccharides and any mixtures thereof. A combination of prebiotics may be used such as 90% GOS with 10% short chain fructo-oligosaccharides such as the product sold under the trademark Raftilose® or 10% inulin such as the product sold under the trademark Raftiline®.

A particularly preferred prebiotic is a mixture of galacto-oligosaccharide(s), N-acetylated oligosaccharide(s) and sialylated oligosaccharide(s) in which the N-acetylated oligosaccharide(s) represent(s) 0.5 to 4.0% of the oligosaccharide mixture, the galacto-oligosaccharide(s) represent(s) 92.0 to 98.5% of the oligosaccharide mixture and the sialylated oligosaccharide(s) represent(s) 1.0 to 4.0% of the oligosaccharide mixture. This mixture is hereinafter referred to as "CMOS-GOS". Advantageously, a composition for use according to the invention contains from 2.5 to 15.0 wt % CMOS-GOS on a dry matter basis with the proviso that the composition comprises at least 0.02 wt % of an N-acetylated oligosaccharide, at least 2.0 wt % of a galacto-oligosaccharide and at least 0.04 wt % of a sialylated oligosaccharide.

WO2006087391 and WO2012160080 provide some examples of production of CMOS-GOS.

Uses of the Nutritional Composition:

The present invention is directed to a nutritional composition comprising a protein source, a lipid source and a carbohydrate source, wherein the protein content is less than 1.8 g/100 kcal for use in administration to an infant born to a non-obese and non-overweight mother in the first year of the life of the infant so as to reduce the risk of developing metabolic syndrome, increased weight gain, increased fat deposition, overweight, obesity, insulin resistance, glucose intolerance or diabetes mellitus later in life.

In the present invention, the infants are born to mothers having a BMI lower than 25.

The present invention also relates to a nutritional composition comprising a protein source, a lipid source and a carbohydrate source, wherein the protein content is less than 1.8 g/100 kcal for use in administration to an infant born to non-obese and non-overweight mothers in the first year of the life of the infant so as to obtain a hormonal profile closer to that of breast fed infants.

By the term "obtain a hormonal profile" is meant to "obtain a content of hormones". The hormones refer especially to IGF-1.

By the term "closer to" in the expression "closer to that of breast fed infants", it is meant that the hormonal profile is closer to that of breast fed infants as compared to the hormonal profile of infants fed with an infant formula having a protein content above 1.8 g/100 kcal, e.g. above 2.0 g/100 kcal, such as 2.1 g/100 kcal. By the term "closer to" it is not meant that the hormonal profile of infants fed with a nutritional composition comprising below 1.8 g/100 kcal protein equals the hormonal profile of breast fed infants, it is simply meant that the hormonal profile is closer to that of breast fed infants than the hormonal profile of infants fed with a standard infant formula (protein above 1.8 g/100 kcal).

A particular embodiment of the invention relates to the use of a nutritional composition comprising a protein source, a lipid source and a carbohydrate source, wherein the protein content is less than 1.8 g/100 kcal for use in administration to an infant born to a non-obese and non-overweight mother in the first year of the life of the infant so as to obtain an IGF-1 level in the infant which is closer to that of breast fed infants than the IGF-1 level in infants fed with a nutritional composition comprising protein in an amount above 1.8 g/100 kcal.

Furthermore, a reduced level of IGF-1 in infants fed with a nutritional composition comprising less than 1.8 g/100 kcal will induce a hormonal profile in the infant closer to the one of a breast fed infant.

The present invention also relates to a nutritional composition comprising a protein source, a lipid source and a carbohydrate source, wherein the protein content is less than 1.8 g/100 kcal for use in administration to an infant born to a non-obese and non-overweight mother in the first year of the life of the infant so as to reduce the protein burden on non-mature organs in the infant.

By the term "reduce protein burden" it is meant reducing the amount of proteins which can cause damage to non-mature organs in an infant, and reducing the burden high amount of proteins can cause.

It is particularly the preterm infants, the low weight infants and the low for gestational age infant who may have problems with cause of damage, protein burden on unmature organs, therefore the infant is in a particularly advantageous embodiment a preterm infant, a low weight infant or a low for gestational age infant.

The present invention also relates to a nutritional composition comprising a protein source, a lipid source and a carbohydrate source, wherein the protein content is less than 1.8 g/100 kcal for use in administration to an infant born to a non-obese and non-overweight mother in the first year of the life of the infant so as to promote a rate of growth in that infant which approximates to the rate of growth of a breast fed infant at the same age.

The term "approximates" refers to a rate of growth which is closer to the one of breast fed infants as compared to the growth rate of an infant fed with a standard nutritional composition comprising above 1.8 g/100 kcal protein. The term "approximates" does not mean that the growth rate has to be equal to that of breast fed infants, it just has to be closer to that of breast fed infants, than the growth rate of infants fed with standard infant formulas are to breast fed infants.

IGF-1 level was measured in blood samples taken from infants by any conventional method, for example a chemi-lumiscence kit (Nichols Advantage, S. Juan Capistrano, Calif., USA).

The connection between IGF-1 and body weight is well known in the art, see for example Savino et al., "*Relationships between IGF-1 and Weight Z score, BMI, Tripital Skin-Fold Thickness, Type of feeding in Healthy Infants in the First 5 months of life*", Ann Nutr Metab 2005, 49, 83-87, where it is disclosed that formula fed infants have a significant higher IGF-1 level and higher body weight than breast fed infants. The document furthermore discloses the relationship between IGF-1 levels and body weight. The inventors of the present invention believe, without being bound by any theory, that infants having a lower IFG-1 level will reduce the risk of obtaining obesity later in life. However, a proposed mechanism of obesity in formula fed infants compared to breast fed infants is that a high protein intake would promote the secretion of IGF-1, a tropical hormone involved in longitudinal growth as well as muscle and fat mass development. Thus, by feeding infants with infant formulas having a lower amount of protein than conventionally infant formulas, the IGF-1 level in the infant is decreased and the risk of obtaining obesity later in life is reduced.

Besides from measuring the IGF-1 level in infants, blood pressure and insulin sensitivity can be measured in order to see an indication of obesity.

Further aspects of the present invention are given as the following items:

1. Use of a protein source, a lipid source and a carbohydrate source for the preparation of a nutritional composition, wherein said composition comprises a protein content of less than 1.8 g/100 kcal for administration to an infant born to non-obese and non-overweight mothers in the first year of the life of the infant so as to reduce risk of develop metabolic syndrome, increased weight gain, increased fat deposition, overweight, obesity, insulin resistance or diabetes mellitus later in said infant's life.
2. Use of a protein source, a lipid source and a carbohydrate source for the preparation of a nutritional composition, wherein said composition comprises a protein content of less than 1.8 g/100 kcal for administration to an infant born to non-obese and non-overweight mothers in the first year of the life of the infant so as to obtain a hormonal profile closer to that of breast fed infants.
3. Use of a protein source, a lipid source and a carbohydrate source for the preparation of a nutritional composition, wherein said composition comprises a protein content of less than 1.8 g/100 kcal for administration to an infant born to non-obese and non-overweight mothers in the first year of the life of the infant so as to reduce the protein burden on non-mature organs in the infant.
4. Use of a protein source, a lipid source and a carbohydrate source for the preparation of a nutritional composition, wherein said composition comprises a protein content of less than 1.8 g/100 kcal for administration to an infant born to non-obese and non-overweight mothers in the first year of the life of the infant so as to promote a rate of growth in that infant which approximates to the rate of growth of a breast fed infant of the same age.
5. The use according to any of the preceding items, wherein the energy density of the composition is from 620 to 680 kcal/litre.
6. The use according to item 5, wherein the energy density of the composition is from 620 to 650 kcal/litre.
7. The use according to item 5, wherein the energy density of the composition is from 650 to 680 kcal/litre.
8. The use according to any of the items 1 to 7, wherein the protein content of the composition is from 1.4 to 1.7 g/100 kcal.
9. The use according to any of the items 1 to 8, wherein the protein source includes casein and/or whey protein.
10. The use according to any of the items 1 to 9, wherein the protein source has a casein to whey ratio from 30:70 to 70:30, preferably 40:60.
11. The use of items 9 or 10, wherein the whey protein is sweet whey from which the caseino-glycomacropeptide has been removed and the nutritional composition additionally includes free phenylalanine in an amount of up to 2.2%, free isoleucine in an amount of up to 0.92%, free tryptophan in an amount of up to 0.34% and free histidine in an amount of up to 0.19%, in each case as a percentage by weight of total protein content.
12. The use according to any of the items 1 to 11, wherein the protein(s) are hydrolysed.
13. The use according to any of the items 1 to 12, wherein the protein(s) are intact.
14. The use according to any of the items 1 to 13, which further includes a probiotic bacterial strain in an amount of from $10^6$ to $10^{11}$ cfu/g of composition (dry weight).

A further aspect of the present invention relates to a method for reducing risk in an infant born to a non-obese and non-overweight mother to develop metabolic syndrome, increased weight gain, increased fat deposition, overweight, obesity, insulin resistance or diabetes mellitus later in said infant's life, the method comprising administering to said infant born to a non-obese and non-overweight mother in the first year of the life of the infant a nutritional composition comprising a protein source, a lipid source and a carbohydrate source and wherein said composition comprises a protein content of less than 1.8 g/100 kcal.

Another aspect of the present invention relates to a method for obtaining in an infant born to a non-obese and non-overweight mother a hormonal profile closer to that of breast fed infants, the method comprising administering to said infant born to a non-obese and non-overweight mother in the first year of the life of the infant a nutritional composition comprising a protein source, a lipid source and a carbohydrate source and wherein said composition comprises a protein content of less than 1.8 g/100 kcal.

Still a further aspect of the present invention relates to a method for reducing the protein burden on non-mature organs in an infant born to a non-obese and non-overweight mother, the method comprising administering to said infant in the first year of the life of the infant a nutritional composition comprising a protein source, a lipid source and a carbohydrate source and wherein said composition comprises a protein content of less than 1.8 g/100 kcal.

Yet another aspect of the present invention relates to a method for promoting a rate of growth in an infant born to a non-obese and non-overweight mother which approximates to the rate of growth of a breast fed infant at the same age, the method comprising administering to said infant born to a non-obese and non-overweight mother in the first year of the life of the infant a nutritional composition comprising a protein source, a lipid source and a carbohydrate source and wherein said composition comprises a protein content of less than 1.8 g/100 kcal.

The nutritional composition of the present invention is administrated to an infant in the first year of the life. It may be administered during this entire specific window of time, or during only a part thereof, for example after the third month of life of the infant such as from 3 to 6 months, or from 3 to 12 months. The administration can start from birth or some days/weeks/months after. The administration can be continuous or not.

It should be noted that the embodiments and features described in the context of one of the aspects of the present invention also apply to the other aspects of the invention.

All patent and non-patent references cited in the present application, are hereby incorporated by reference in their entirety.

The invention will now be described in further details in the following non-limiting example.

EXAMPLE

The following example illustrates a specific embodiment of the infant formula for use according to the present invention. The example is given solely for the purpose of illustration and is not to be construed as limitations of the present invention, as many variations thereof are possible without departing from the spirit of the invention.

Example 1

Example 1 describes a study conducted to study infants being fed with an infant formula having a low amount of protein, 1.61 g/100 kcal, (test formula) as compared to a conventional infant formula having a protein content of 2.15 g/100 kcal (control formula).

The primary objective of the study was to evaluate the growth of the infants and measure the IGF-1 level in the infants at an age of both 6 months and 12 months after birth.

Both the test formula and the control formula were prepared as a ready-to-feed liquid (they were produced as a powder then prepared as a ready-to-feed liquid for the administration to the infants). The two formulas, test formula and control formula, once reconstituted, are described below in table 1.

TABLE 1

|  | Test formula | Control formula |
| --- | --- | --- |
| Energy (kcal/100 ml) | 67.2 | 64.6 |
| Protein (g/100 kcal) | 1.61 | 2.15 |
| Hydrolization | Intact protein | Intact protein |
| Whey:casein ratio | 60:40 | 60:40 |
| CHO (g/100 kcal) (*) | 11.1 | 11.13 |
| CHO (type) (*) | Lactose | Lactose + syrup (corn syrup) |
| Fat (g/100 kcal) | 5.46 | 5.21 |
| Fat (type) | Palm olein, soybean, coconut, safflower oils | Palm olein, soybean, coconut, safflower oils, sunflower oils |
| Linoleic/α-linolenic acid | 11.3 | 9.6 |
| LC-PUFAs () | DHA/ARA 1:2 (*) | DHA/ARA 1:2 (***) |

(*) CHO refers to carbohydrate
(**) LC-PUFAs refers to long chain polyunsaturated fatty acids
(***) DHA refers to docosahexaenoic acid and ARA refers to arachidonic acid The formulas above were fed to infants as the sole nutrition from the age of three months to six months and subsequently as part of a mixed diet during the introduction of solid foods to the infant until weaning is complete at about the age of 12 months.

The mothers of the infants in this study came from a normal population and therefore contained women which had a normal distribution of weight. In table 2 below, the BMI are shown for the mothers of the infants in the study. The BMI is a measure for the weight of the women and the BMI of the mothers are before pregnancy.

TABLE 2

|  | Mothers to infants fed with formula | Mothers of infants breast fed |
| --- | --- | --- |
| BMI <25 | 46% | 65% |
| BMI 25-30 | 23% | 25% |
| BMI >30 | 31% | 10% |

Thus, almost half of the women in the study had a normal weight (BMI<25) and the other half women were either overweight or obese.

The infants in both the test group and the control group were fed with a conventional infant formula, control formula, up to the age of three months having a protein content of about 2.15 g/100 kcal.

After the age of three months the test group were fed with the test formula and the control group continued being fed with the control formula. After the age of 6 months the infants were fed with the infant formulas, control formula and test formula, but also with solid foods.

The infants in the test group, the control group and the group of infants breast fed were evaluated at 6 months from birth and at 12 months from birth. Their body weight, length, head circumference, and abdominal skinfold were measured. Besides, a blood sample was taken and IGF-1 measured.

The study showed that the infants fed with the test formula (protein content 1.61 g/100 kcal) had a lower weight gain from 3 to 6 months than infants fed with the control formula (protein content 2.15 g/100 kcal).

For example, the difference in the weight gain between the test group and the control group was calculated to be −0.71 g/day, calculated as [average weight gain of test group per day from 3 to 6 months] minus [average weight gain of control group per day from 3 to 6 months]. This clearly shows that an infant fed with a low amount of protein compared to a higher amount of protein will have a lower weight gain, almost 1 gram per day (−0.71 g/day) lower.

The results also showed that the difference in the weight gain between the test group and the control group from 3 to 12 months were −231 g (or −0.80 g/day).

The study very surprisingly also showed that the differences in weight gain of infants from 3 to 6 months and from 3 to 12 months between the test group and control group were higher the lower the BMI of the infant's mother were, i.e. infants from normal weight mothers (BMI<25) had a higher difference in weight gain between control group and test group than infant of obese mothers.

For example, between 3 and 6 months the weight gain is −1.27 g/day for infants born to mothers having a BMI lower than 25, whereas it is −0.45 g/day for those born to mothers being overweight or obese (BMI equals or higher than 25).

In table 3 below, the differences in weight gain between the test group and the control group in relation to the BMI of the infant's mothers are shown. It was very surprising to the inventors of the present invention to see this decrease in weight gain of infants in the test group compared to infants in the control group in relation to a decrease in BMI of the infant's mother.

TABLE 3

|  | From 3 to 6 months | From 3 to 12 months |
| --- | --- | --- |
| Weight gain (g/day) In total ΔTest group-control group | −0.71 | −0.80 (−231 g) |

TABLE 3-continued

|  | From 3 to 6 months | From 3 to 12 months |
|---|---|---|
| Weight gain (g/day) BMI <25 ΔTest group-control group | −1.27 | −1.02 |
| Weight gain (g/day) BMI: > or =25 ΔTest group-control group | −0.45 | −0.64 |

The study also very surprisingly showed that the IGF-1 level in infants fed with the test formula was lower than the IGF-1 levels in infants fed with control infant formula both when the infant was 6 months and 12 months. The IGF-1 level of infants in the study is shown below in table 4.

TABLE 4

| IGF-1 at 6 months Δ test group-control group | −11.03% |
|---|---|
| IGF-1 at 12 months Δ test group-control group | −15.74% |
| IGF-1 at 6 months Δ test group- group of breast fed infant | 63.18% |
| IGF-1 at 12 months Δ test group- group of breast fed infant | 17.86% |
| IGF-1 at 6 months Δ group of breast fed infant-control group | −65.50% |
| IGF-1 at 12 months Δ group of breast fed infant-control group | −24.90% |

Thus, from the above table, it is evident that the IGF-1 level is lower in infants in the test group than in the control group, both when the infant is 6 months and 12 months. Thus, the data clearly shows that infants fed with an infant formula comprising 1.61 g/100 kcal protein has a lower IGF-1 level than infants fed with an infant formula comprising from 2.15 g/100 kcal protein. Further, table 4 shows that the IGF-1 level in infants fed with an infant formula comprising a low amount of protein (1.61 g/100 kcal) is closer to that of breast fed infants than the IGF-1 level in infants fed with an infant formula comprising a higher amount of protein (2.15 g/100 kcal). Thus, the hormonal profile of infants in the test group is closer to that of breast fed infants than for the infants in the control group.

The invention claimed is:

1. A method for obtaining a hormonal profile closer to that of breast fed infants in an infant born to a non-obese and non-overweight mother and fed formula, the method comprising administering a nutritional composition comprising a protein source, a lipid source and a carbohydrate source, wherein the protein content is less than 1.8 g/100 kcal, and the nutritional composition is administered to the infant born to the non-obese and non-overweight mother, in the first year of the life of the infant, wherein the protein source comprises sweet whey from which caseino-glycomacropeptide has been removed; the nutritional composition includes free phenylalanine, free isoleucine, free tryptophan, and free histidine; and the free phenylalanine is present in an amount of up to 2.2%, the free isoleucine is present in an amount of up to 0.92%, the free tryptophan is present in an amount of up to 0.34%, and the free histidine is present in an amount of up to 0.19%, in each case as a percentage by weight of total protein content.

2. A method for reducing a protein burden on non-mature organs in an infant born to a non-obese and non-overweight mother, the method comprising administering a nutritional composition comprising a protein source, a lipid source and a carbohydrate source, wherein the protein content is less than 1.8 g/100 kcal, and the nutritional composition is administered to the infant born to the non-obese and non-overweight mother, in the first year of the life of the infant, wherein the protein source comprises sweet whey from which caseino-glycomacropeptide has been removed; the nutritional composition includes free phenylalanine, free isoleucine, free tryptophan, and free histidine; and the free phenylalanine is present in an amount of up to 2.2%, the free isoleucine is present in an amount of up to 0.92%, the free tryptophan is present in an amount of up to 0.34%, and the free histidine is present in an amount of up to 0.19%, in each case as a percentage by weight of total protein content.

3. A method for promoting a rate of growth in a non-breast fed infant born to a non-obese and non-overweight mother, which approximates to the rate of growth of a breast fed infant of the same age, the method comprising administering a nutritional composition comprising a protein source, a lipid source and a carbohydrate source, wherein the protein content is less than 1.8 g/100 kcal, and the nutritional composition is administered to the non-breast fed infant born to the non-obese and non-overweight mother, in the first year of the life of the non-breast fed infant, wherein the protein source comprises sweet whey from which caseino-glycomacropeptide has been removed; the nutritional composition includes free phenylalanine, free isoleucine, free tryptophan, and free histidine; and the free phenylalanine is present in an amount of up to 2.2%, the free isoleucine is present in an amount of up to 0.92%, the free tryptophan is present in an amount of up to 0.34%, and the free histidine is present in an amount of up to 0.19%, in each case as a percentage by weight of total protein content.

4. The method according to claim 1, wherein the composition has an energy density of the composition from 600 to 680 kcal/litre.

5. The method according to claim 1, wherein the composition has an energy density of the composition from 620 to 650 kcal/litre.

6. The method according to claim 1, wherein the composition has an energy density of the composition from 650 to 680 kcal/litre.

7. The method according to claim 1, wherein the protein content of the composition is from 1.4 to 1.7 g/100 kcal.

8. The method according to claim 1, wherein the protein source further includes a casein and/or another whey protein.

9. The method according to claim 1, wherein the protein source further includes a casein.

10. The method according to claim 9, wherein the protein source has a casein to whey ratio from 30:70 to 70:30.

11. The method according to claim 1, wherein the protein source is fully or partially hydrolysed proteins.

12. The method according to claim 1, wherein the protein source is intact proteins.

13. The method according to claim 1, wherein the composition includes a probiotic strain in an amount of from $10^6$ to $10^{11}$ cfu/g of composition (dry weight).

14. The method according to claim 2, wherein the composition has an energy density of the composition from 600 to 680 kcal/litre.

15. The method according to claim 2, wherein the composition has an energy density of the composition from 620 to 650 kcal/litre.

16. The method according to claim 2, wherein the composition has an energy density of the composition from 650 to 680 kcal/litre.

17. The method according to claim 2, wherein the protein content of the composition is from 1.4 to 1.7 g/100 kcal.

18. The method according to claim 2, wherein the protein source includes a casein and/or another whey protein.

19. The method according to claim 2, wherein the protein source further includes a casein.

20. The method according to claim 19, wherein the protein source has a casein to whey ratio from 30:70 to 70:30.

21. The method according to claim 2, wherein the protein source is fully or partially hydrolysed proteins.

22. The method according to claim 2, wherein the protein source is intact proteins.

23. The method according to claim 2, wherein the composition includes a probiotic strain in an amount of from $10^6$ to $10^{11}$ cfu/g of composition (dry weight).

24. The method according to claim 3, wherein the composition has an energy density of the composition from 600 to 680 kcal/litre.

25. The method according to claim 3, wherein the composition has an energy density of the composition from 620 to 650 kcal/litre.

26. The method according to claim 3, wherein the composition has an energy density of the composition from 650 to 680 kcal/litre.

27. The method according to claim 3, wherein the protein content of the composition is from 1.4 to 1.7 g/100 kcal.

28. The method according to claim 3, wherein the protein source includes a casein and/or another whey protein.

29. The method according to claim 3, wherein the protein source further includes a casein.

30. The method according to claim 29, wherein the protein source has a casein to whey ratio from 30:70 to 70:30.

31. The method according to claim 3, wherein the protein source is fully or partially hydrolysed proteins.

32. The method according to claim 3, wherein the protein source is intact proteins.

33. The method according to claim 3, wherein the composition includes a probiotic strain in an amount of from $10^6$ to $10^{11}$ cfu/g of composition (dry weight).

* * * * *